(12) United States Patent
Clemens et al.

(10) Patent No.: US 7,184,839 B2
(45) Date of Patent: Feb. 27, 2007

(54) CATHETER-DELIVERED CARDIAC LEAD

(75) Inventors: Willim J. Clemens, Fridley, MN (US);
Michael L. Freiborg, New Hope, MN (US); Michael A. Ruff, Blaine, MN (US); Douglas N. Hess, Maple Grove, MN (US); Elisabeth L. Belden, Maple Grove, MN (US); Terrell M. Williams, Brooklyn Park, MN (US); Brian T. McHenry, Minneapolis, MN (US); Mark B. Bucheger, Andover, MN (US); Timothy G. Laske, Shoreview, MN (US); Matthew D. Bonner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 624 days.

(21) Appl. No.: 10/318,518

(22) Filed: Dec. 16, 2002

(65) Prior Publication Data

US 2004/0116993 A1    Jun. 17, 2004

(51) Int. Cl.
*A61N 1/05* (2006.01)
(52) U.S. Cl. .................. 607/120; 607/122; 607/127; 607/116
(58) Field of Classification Search ........ 607/119–120, 607/122, 126–128
See application file for complete search history.

(56) References Cited

U.S. PATENT DOCUMENTS

| 5,246,014 | A | 9/1993 | Williams et al. |
| 5,431,681 | A * | 7/1995 | Helland ............ 607/4 |
| 5,447,533 | A * | 9/1995 | Vachon et al. ............ 607/120 |
| 5,571,158 | A | 11/1996 | Bolz et al. |
| 5,654,030 | A | 8/1997 | Munshi et al. |
| 5,760,341 | A | 6/1998 | Laske et al. |
| 5,851,226 | A | 12/1998 | Skubitz et al. |
| 5,987,746 | A | 11/1999 | Williams |
| 6,052,625 | A | 4/2000 | Marshall |
| 6,408,213 | B1 | 6/2002 | Bartig et al. ............ 607/122 |
| 6,430,447 | B1 | 8/2002 | Chitre et al. |
| 6,430,448 | B1 | 8/2002 | Chitre et al. |
| 6,687,550 | B1 * | 2/2004 | Doan ............ 607/127 |
| 2005/0149146 | A1 * | 7/2005 | Boveja et al. ............ 607/58 |

* cited by examiner

*Primary Examiner*—Carl Layno
(74) *Attorney, Agent, or Firm*—Michael C. Soldner; Girma Wolde-Michael

(57) ABSTRACT

A lead for delivering electrical signals to and/or receive electrical signals from a human heart that includes a solid inner conductor, and a fixation device having a titanium nitride coated surface and electrically coupled to the inner conductor. A steroid is applied to the titanium nitride surface of the fixation device, and at least one layer of insulation is positioned around the inner conductor. A conductive coil is positioned around and is insulated from the inner conductor, an electrode ring electrically coupled to the conductive coil is positioned around and is electrically isolated from the inner conductor, and an insulating spacer is positioned between and electrically isolates the ring electrode and the fixation device.

43 Claims, 13 Drawing Sheets

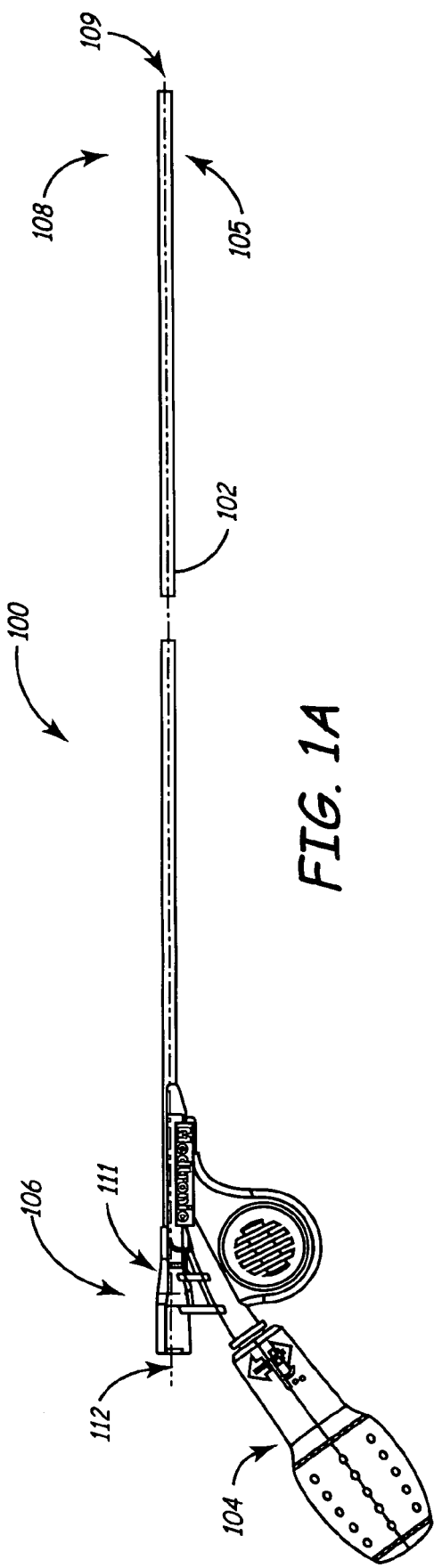
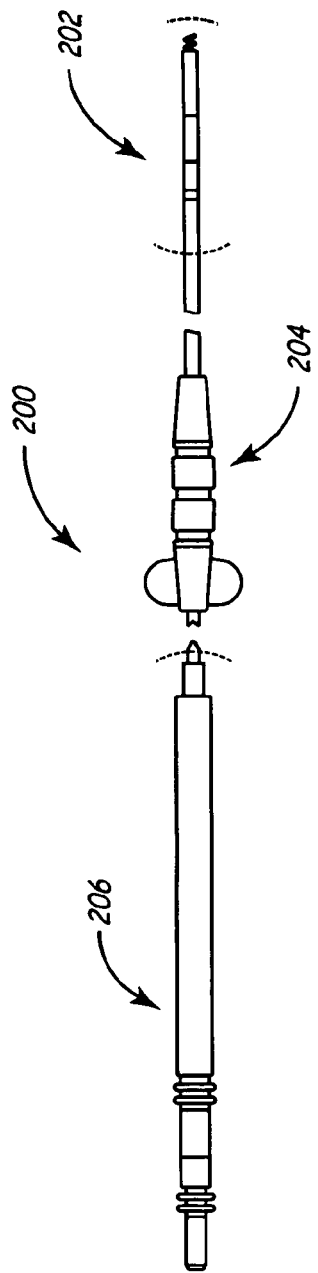
FIG. 1A
FIG. 2A

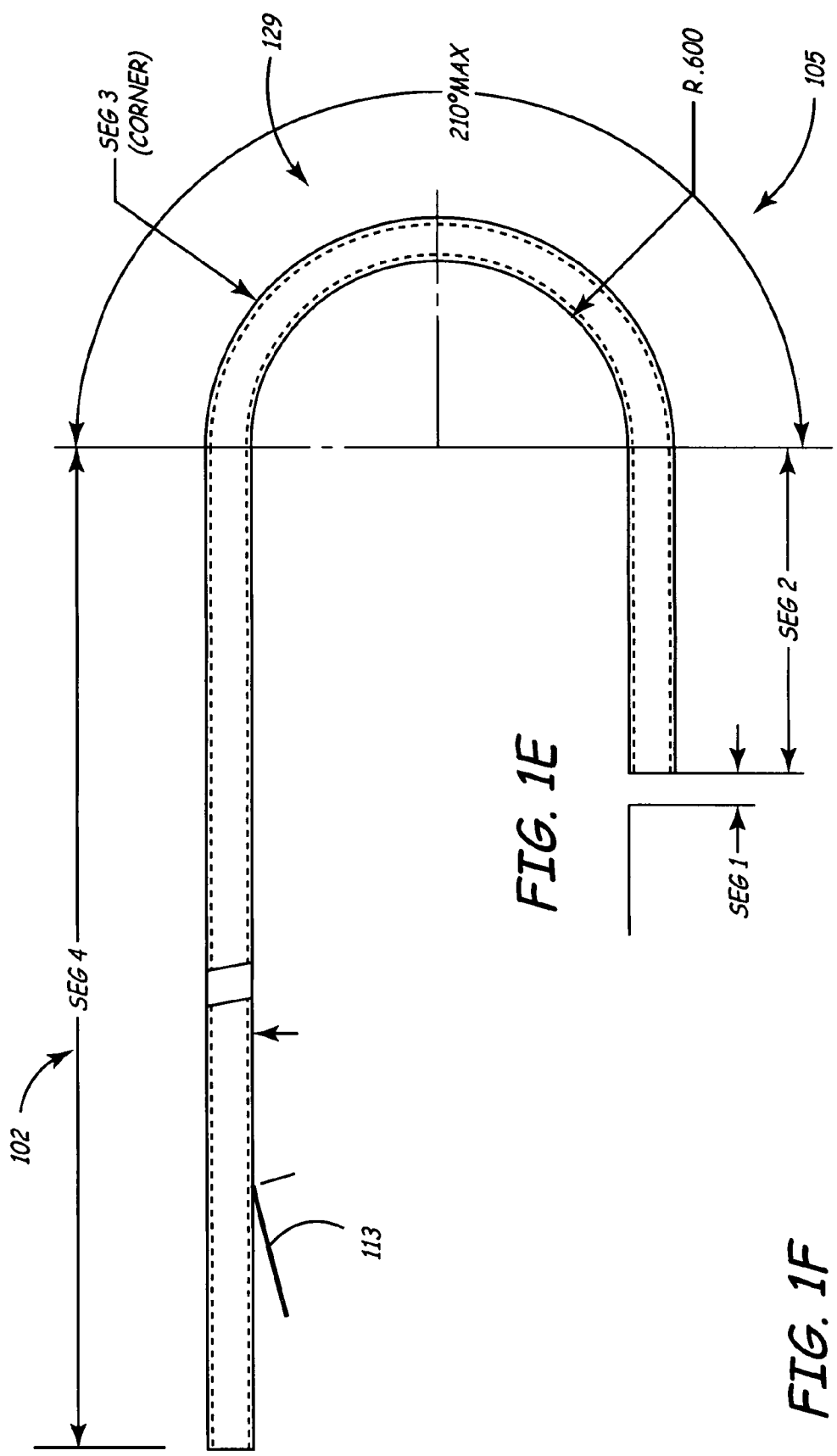

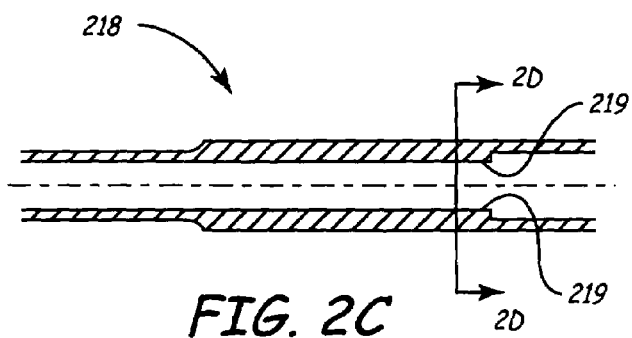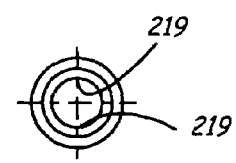
FIG. 2C  FIG. 2D
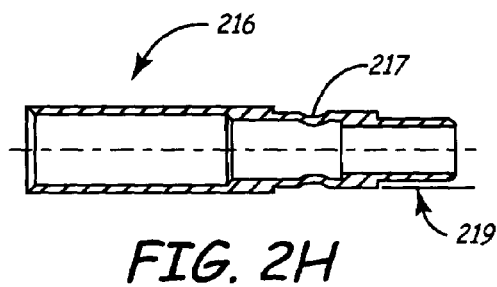
FIG. 2H
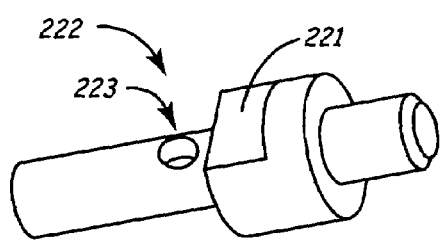
FIG. 2E
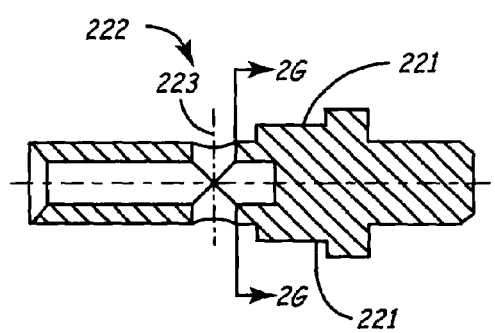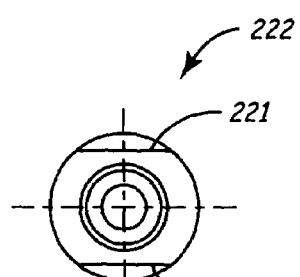
FIG. 2F  FIG. 2G

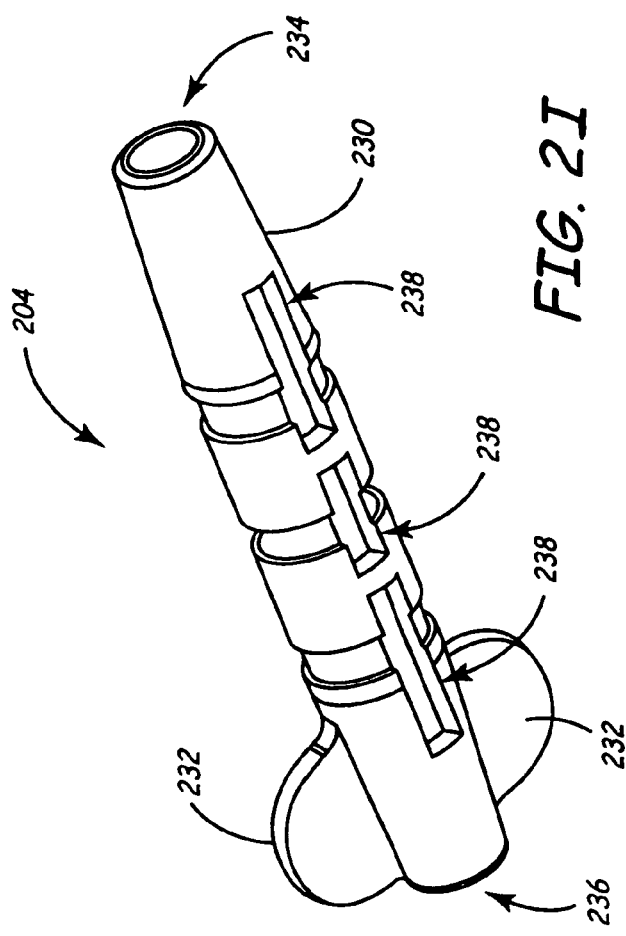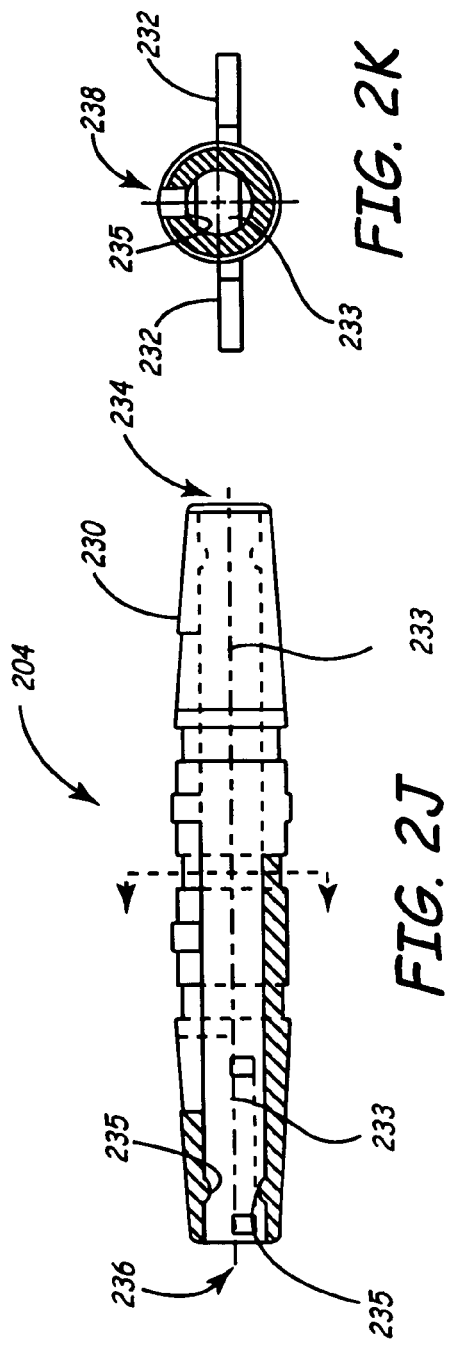

CATHETER-DELIVERED CARDIAC LEAD

FIELD OF THE INVENTION

The present invention is generally directed to implantable medical devices, and, more particularly, the present invention is directed to a catheter-delivered cardiac lead and various methods of placing heart leads in a human heart.

DESCRIPTION OF THE RELATED ART

In pacemaker technology and related arts, a pacemaker and a pacing lead are implanted in a patient. Typically, an electrode is provided at the distal end of the pacing lead, and is adapted to be secured or affixed within the heart. The electrode may have a variety of shapes, e.g., a helical screw, a barb, etc. Pacing leads are commonly implanted with the aid of a stylet that is positioned within a lumen formed in the lead. The stylet is stiff relative to the lead and it thus provides additional rigidity to the lead during advancement of the lead within the patient.

However, despite its success, stylet delivery of pacing leads is, more or less, a trial and error procedure that may, in some cases, have to be repeated one or more times to properly locate the electrode within the heart. That is, with stylet delivery systems, the surgeon or clinician makes an initial estimation or guess as to how to bend the stylet such that the pacing lead will be directed to the desired location within a patient's body. Thereafter, the stylet is inserted in the lead lumen, and the lead is advanced toward the heart by the surgeon. Once the lead is advanced into the heart, e.g., the right atrium or the right ventricle of the heart, the surgeon continues to advance the lead and, in some cases, rotate the lead in an effort to reach the desired area of connection to the heart, i.e., the desired pacing site. If the bend of the stylet does not allow placement of the lead at a location deemed acceptable by the surgeon, the lead must be removed, the stylet must be reshaped, and re-inserted into the heart in an attempt to locate the conductor at the appropriate location. This process continues until the lead is properly positioned at a site deemed acceptable to the clinician or surgeon within the heart. At that point, the electrode is secured to the heart by a variety of techniques, e.g., rotation of a helical screw electrode.

Pacing leads may also be implanted through use of a catheter. One such illustrative technique is disclosed in U.S. Pat. No. 5,851,226, in which a pacing lead is inserted into a lumen within a guide catheter. Thereafter, the guide catheter is advanced to the desired area within the heart. However, such catheters are of a fixed shape, and once positioned within the desired heart chamber, there is limited ability to manipulate the end of the catheter to a desired location within the heart. A stylet-delivered lead is sometimes employed with such catheters using the trial and error procedure described above to position the lead in the desired area within the heart.

Such trial and error procedures can be time-consuming and may result in placement of pacing leads at less than preferred locations. For example, given the nature of the process, the surgeon may reach a conclusion that the pacing lead is positioned sufficiently close to a preferred location. That is, the surgeon may come to the conclusion that, although the lead is not perfectly located, it is as close as possible given the techniques employed for locating the lead.

Moreover, using existing techniques, most pacing leads positioned within the right ventricle of the heart are affixed to the apex of the heart in the right ventricle. This is because that location is relatively easy to access using existing techniques, and adequate pacing and other forms of heart stimulation may be performed from that location. Leads may also be positioned in one of the cardiac veins of the heart, e.g., the great cardiac vein, the middle cardiac vein, the posterial lateral cardiac vein, the anterior lateral cardiac vein, etc., by accessing the coronary sinus in the heart. However, it may be desirable to locate pacing leads, or other types of leads, at other locations within the heart for various reasons. For example, it may be desirable to locate such leads in the right ventricular outflow tract (RVOT), the Bundle of His, etc., as such alternates may enhance the effectiveness of the heart therapy delivered to such sites.

The present invention is directed to overcoming, or at least reducing the effects of, one or more of the problems described above.

SUMMARY OF THE INVENTION

In one aspect, the present invention is directed to lead for delivering electrical signals to and receiving electrical signals from a patient that includes a solid inner conductor and a distal electrode, having a coated surface electrode, electrically coupled to the inner conductor. An anti-inflammatory agent is applied to the distal electrode. At least one layer of insulation is positioned around the inner conductor, a conductive coil is positioned around and insulated from the inner conductor, and a proximal electrode, electrically coupled to the conductive coil, is positioned around and electrically isolated from the inner conductor. An insulating spacer is positioned between and electrically isolating the proximal electrode and the fixation device.

According to an embodiment of the present invention, a lead for delivering electrical signals to and receiving electrical signals from a patient includes a solid inner conductor and a helical screw fixation device, having a first titanium nitride coated surface, electrically coupled to the inner conductor. A steroid is applied to the titanium nitride coated surface of the helical screw fixation device, a fluoropolymer coating is positioned around the inner conductor, wherein the fluoropolymer coating is one of ETFE and PTFE. A layer of insulation is positioned around the fluoropolymer coating, wherein the layer of insulation is one of silicone and polyurethane. A conductive coil, electrically isolated from the inner conductor, is positioned around the layer of insulation, and an electrode ring, having a second titanium nitride coated surface, is positioned around and electrically isolated from the inner conductor and is electrically coupled to the conductive coil. An insulating spacer is positioned between and electrically isolates the electrode ring and the fixation device.

In another aspect, the present invention is directed to a method of forming a lead that includes coupling a fixation device to a solid inner conductor by welding the fixation device to a coupling device that is coupled to the solid inner conductor, forming a titanium nitride coating on a surface of the fixation device, and applying a steroid to the titanium nitride coated surface of the fixation device. At least one layer of insulation is formed around the inner conductor. A conductive coil is positioned around the at least one layer of insulation, an electrode ring is positioned around the inner conductor and is electrically isolated from the inner conductor and electrically coupled to the conductive coil, and an insulating spacer is positioned between the electrode ring and the fixation device

BRIEF DESCRIPTION OF THE DRAWINGS

The invention may be understood by reference to the following description taken in conjunction with the accompanying drawings, in which like reference numerals identify like elements, and in which:

FIG. 1A is a schematic diagram of a steerable catheter according to the present invention;

FIGS. 1E and 1F are, respectively, a top view and a side view of the shaft 102 and the articulatable tip 105 of the catheter 100;

FIG. 2A is a schematic diagram of a lead that may be used with the present invention;

FIGS. 2C and 2D are, respectively, a cross-sectional side view and end view of a spacer of a lead according to the present invention;

FIGS. 2E, 2F and 2G are, respectively, a perspective view, a cross-sectional side view, and an end view of a weld core crimp sleeve of a lead according to the present invention;

FIG. 2H is a cross-sectional side view of an illustrative electrode ring 216 that may be employed with the present invention;

FIGS. 2I, 2J and 2K are, respectively, a perspective view, a cross-sectional side view and an end view of one illustrative embodiment of the anchoring sleeve 204 that may be used with the present invention;

Figure 1B:
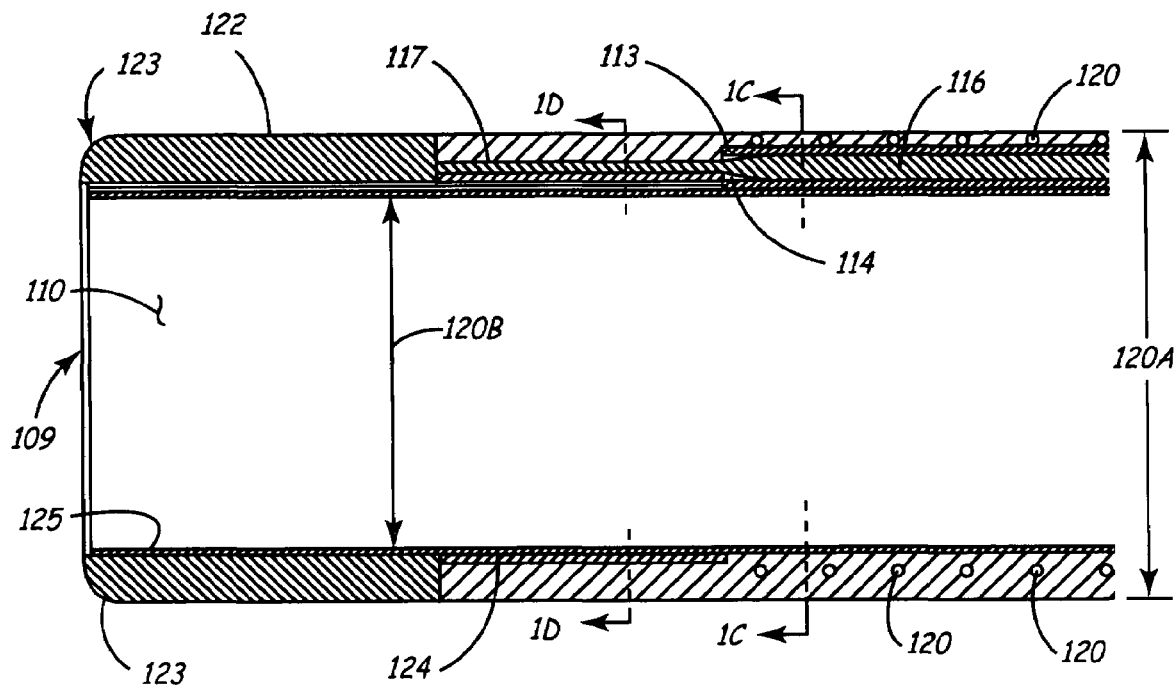
FIG. 1B is a sectional view of a distal end of the steerable catheter of FIG. 1A.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. The relative sizes of the various features and structures depicted in the drawings may be exaggerated or reduced as compared to the size of those features or structures on real-world devices. Moreover, for purposes of clarity, the devices depicted herein may not include all of the detailed components of a real-world implantable medical device. Nevertheless, the attached drawings are included to describe and explain illustrative examples of the present invention.

In general, the present invention is directed to various methods of locating a lead within a human heart by means of various devices disclosed herein. More particularly, in one embodiment, the present invention is directed to positioning a lead within the heart using a steerable catheter having an articulatable tip, and a lead adapted to be positioned within the catheter. The present invention is also directed to a novel lead that may be employed in practicing the methods disclosed herein. Although various specific details are disclosed in describing the subject matter disclosed herein, the present invention should not be considered as limited to such details unless such details are specifically recited in the appended claims. Moreover, as will be understood by those skilled in the art after a complete reading of the present application, the present invention is not limited to the placement of cardiac pacing leads. Rather, the present invention may be used in placing any type of lead that provides electrical stimulation to and/or senses electrical signals from a patient's heart, e.g., defibrillating leads.

Figures 1C, 1D:
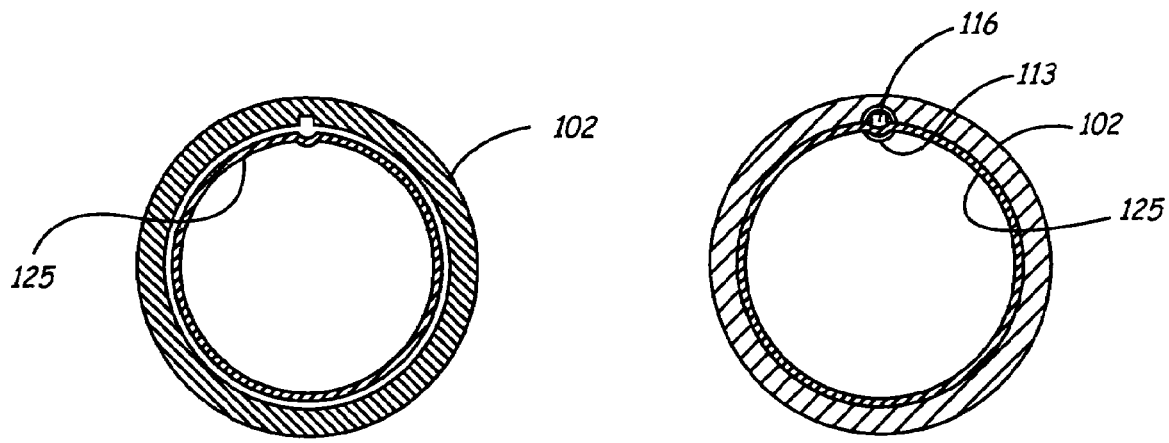
FIG. 1C is a cross-sectional view of a distal end of a steerable catheter according to the present invention, taken along cross-sectional lines 1C—1C of FIG. 1B.
FIG. 1D is a cross-sectional view of a distal end of a steerable catheter according to the present invention, taken along cross-sectional lines 1D—1D of FIG. 1B.

One illustrative embodiment of a steerable catheter 100 that may be employed with the present invention is depicted in FIGS. 1A–1D. FIG. 1A is a schematic diagram of a steerable catheter according to the present invention. As illustrated in FIG. 1A, a catheter 100 include a shaft 102, an actuatable handle 104, a shaft housing 111, an articulatable tip 105, a proximal end 106, a distal end 108, and a distal opening 109. FIG. 1B is a sectional view of a distal end of the steerable catheter of FIG. 1A. FIG. 1C is a cross-sectional view of a distal end of a steerable catheter according to the present invention, taken along cross-sectional lines 1C—1C of FIG. 1B. FIG. 1D is a cross-sectional view of a distal end of a steerable catheter according to the present invention, taken along cross-sectional lines 1D—1D of FIG. 1B. As illustrated in FIGS. 1A–1D, the shaft 102 has a main lumen 110 that is adapted to have a lead 200 (see FIG. 2A) positioned therein. The lead 200 may be inserted through a proximal opening 112 on the proximal end 106 of the shaft 102. The shaft 102 may be positioned within and extend through a lumen (not shown) in the shaft housing 111 and secured therein by an appropriate adhesive material or in situ-molded directly onto the shaft 102. The shaft housing 111 may be formed of a variety of materials, such as urethane, and may be of an extruded and fused construction.

In general, as described more fully below, by actuating the handle 104, the distal end 108 of the shaft 102 is manipulated to a variety of locations, thereby allowing more accurate placement of the lead 200 at a variety of locations within a human heart. The catheter shaft 102 may be configured so that it may be slit or cut when being removed from a patient. However, as will be understood after a complete reading of the present application, the catheter 100 and methods disclosed herein may be practiced with leads of various construction and purpose. Thus, the present invention should not be considered as limited to use with the illustrative lead 200 depicted herein.

As illustrated in FIGS. 1B–1D, the catheter 100 includes a PTFE lined, wire-braided tubing member 113 that defines a pull wire lumen 114 adapted to have a pull wire 116 positioned therein. The outer diameter 120A and inner diameter 120B of the shaft 102 may vary. In one illustrative embodiment, the shaft 102 has an overall length of approximately 21 inches, an inner diameter 120B of approximately 0.100 inches, and an outer diameter 120A of approximately 0.129 inches. The lined, wire-braided tubing member 113 may have an inner diameter of approximately 0.0085 inches and an outer diameter of approximately 0.012 inches. Thus, the pull wire lumen 114 has an inner diameter of approximately 0.0085 inches. The pull wire 116 may be a wire formed of type 304 stainless steel, and may have a diameter of approximately 0.007 inches.

The shaft 102 may be a composite structure including, for example, a PTFE inner liner, a wire-braided structure surrounding the PTFE liner, and an outer polymer jacket, formed of, for example, a polymer, such as PEBAX. The stiffness of the shaft 102 may vary along its length. For example, the stiffness, as referenced by the diameter hardness, may vary from approximately 35D–72D (Shore D scale), with the shaft being more flexible (softer) toward the distal end. When the shaft 102 is manufactured, a material, such as barium sulfate, may be introduced into the polymer outer jacket such that the shaft 102 may be more radiopaque, thereby making it easier to observe during use. In one embodiment, the shaft 102 includes braided wire material 120 formed in the shaft 102. In one illustrative embodiment, the braided metal is a continuous pattern of 8×8 round medium tensile wires having a diameter of approximately 0.002 inch. The shaft 102 includes a relatively soft end 122 (approximately 35D) made of a polymer, such as PEBAX. The end 122 may have an axial length of approximately 0.100 inches. The shaft 102 also includes a band 124 made of an radiopaque material, such as gold, and a liner 125 formed of a polymer, such as PTFE, ETFE, HDPE, etc. The corners 123 of the end 122 may be rounded, and the liner 125 may be slightly recessed within the end 122.

The shaft 102 may be manufactured using traditional reflow manufacturing techniques over an assembly mandrel. That is, the liner 125 is positioned over a mandrel (not shown), and the various components of the shaft 102, e.g., the band 124, the lined braided tubing member 113, having the pull wire 116 positioned therein, and the braided wire material 120, are all positioned around the liner 125. Thereafter, the shaft material, e.g., PEBAX, is applied to this structure and heated and reflowed to result in the structure depicted in the attached drawings. Note that the end 117 of the pull wire 116 is attached to the band 124.

FIGS. 1E and 1F are, respectively, a top view and a side view of the shaft 102 and the articulatable tip 105 of the catheter 100. As illustrated in FIGS. 1E–1F, the shaft 102 includes multiple segments, e.g., segments SEG1–SEG4, the length and hardness of which may be varied to accomplish certain desired results, e.g., desired curvature radius, desired tip stiffness, etc. For example, the length of the segment SEG4 may be adjusted as desired. The length of segment SEG3 may be adjusted to control the radius ("R") of the bend 129 of the shaft 102. Additionally, the radius of curvature of the bend 129 may be controlled by adjusting the hardness of the material forming the shaft 102. In one illustrative embodiment, the shaft 102 is bent or deflected up through a maximum of approximately 210 degrees. The lateral reach of the catheter 100 is set by adjusting the length of the segment SEG2. The segment SEG1 is indicative of the axial length of the end 122. In one illustrative embodiment, segment SEG1 is approximately 0.100 inches in length, segment SEG2 is approximately 1.0 inches in length, the radius of segment SEG3 is approximately 0.600 inches, and the length of segment SEG4 is approximately 18–20 inches. The braided tubing 113, that defines the pull wire lumen, exits the shaft 102 via opening 119 formed in the shaft 102. As described more fully below, the pull wire 116 positioned within the braided tubing 113 is coupled to the handle 104.

Figure 1G:
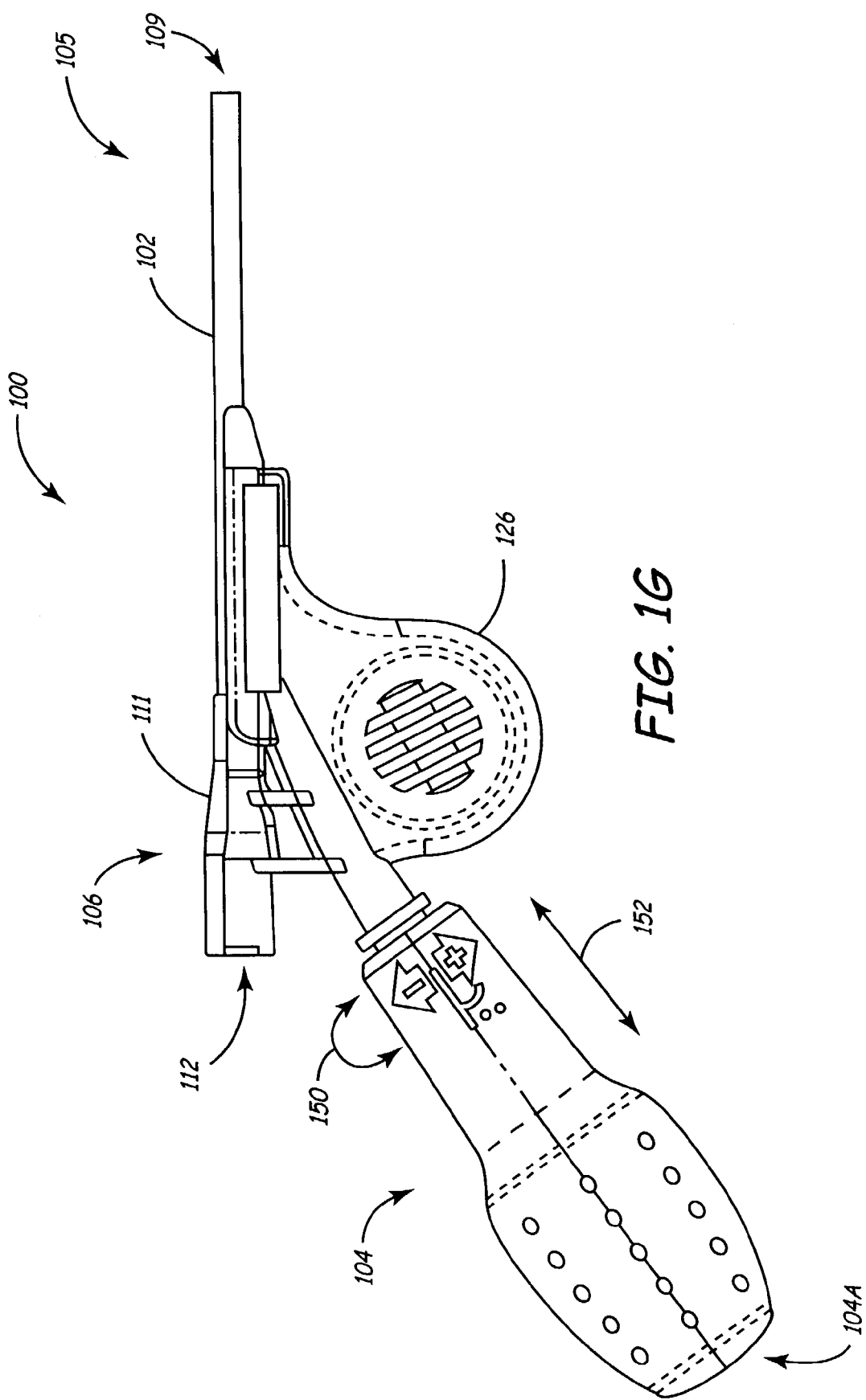
FIG. 1G is an enlarged side view of a handle of a steerable catheter according to the present invention.
Figure 1H:
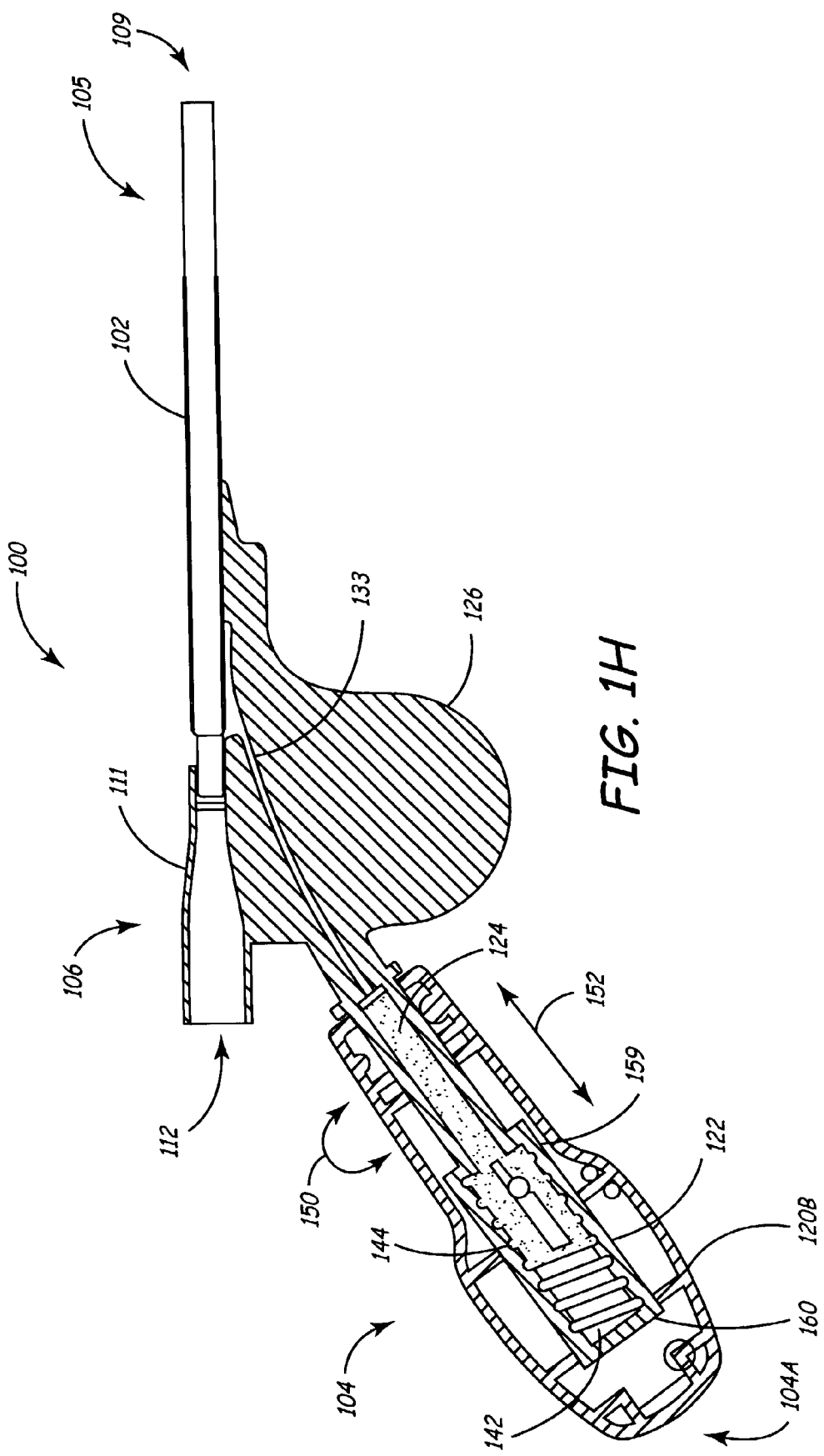
FIG. 1H is a cross-sectional side view of a handle with an articulatable tip in a straight or extended position.
Figure 1I:
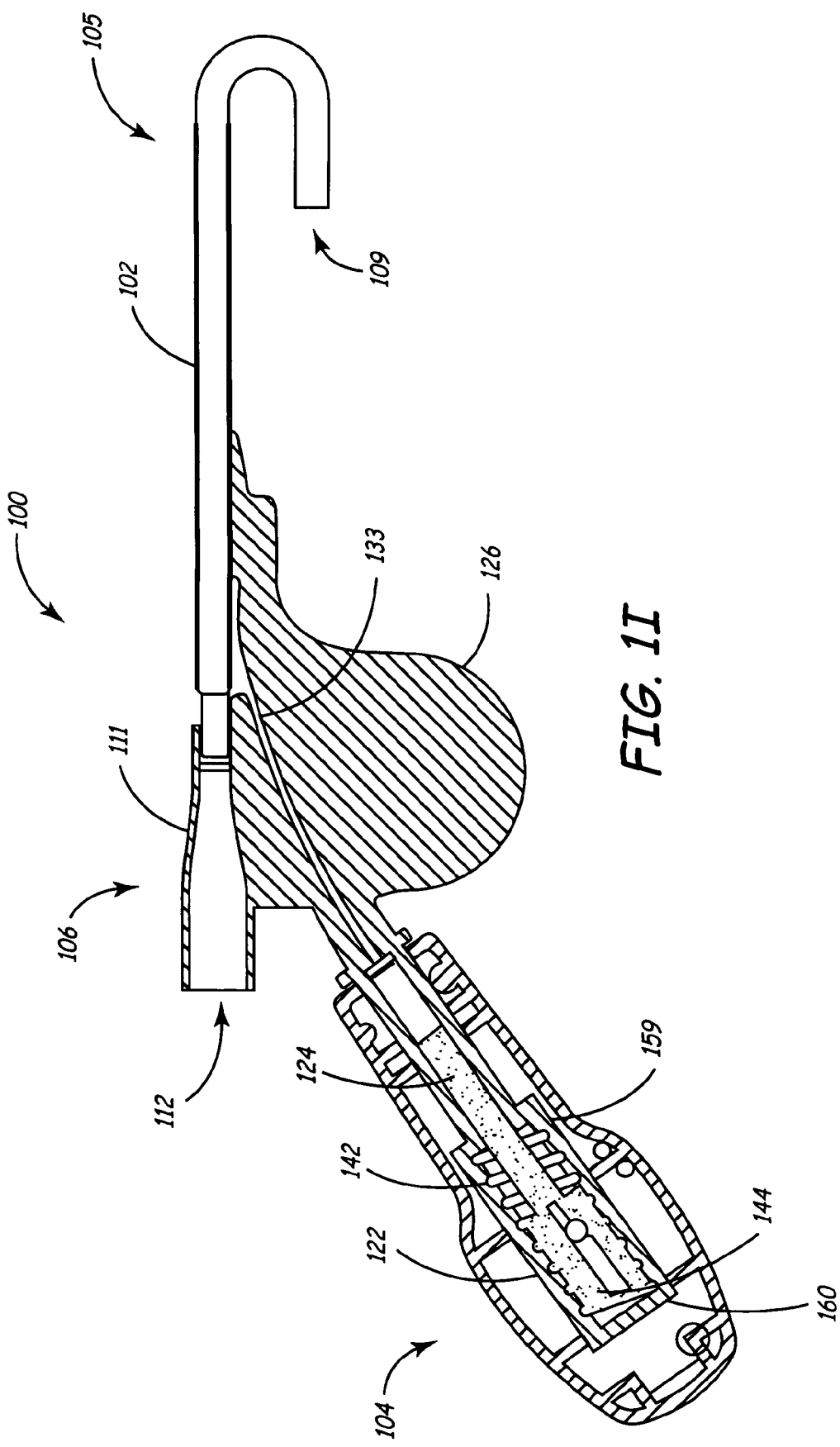
FIG. 1I is a cross-sectional view of a handle with a tip in a fully articulated position.
Figure 1J:
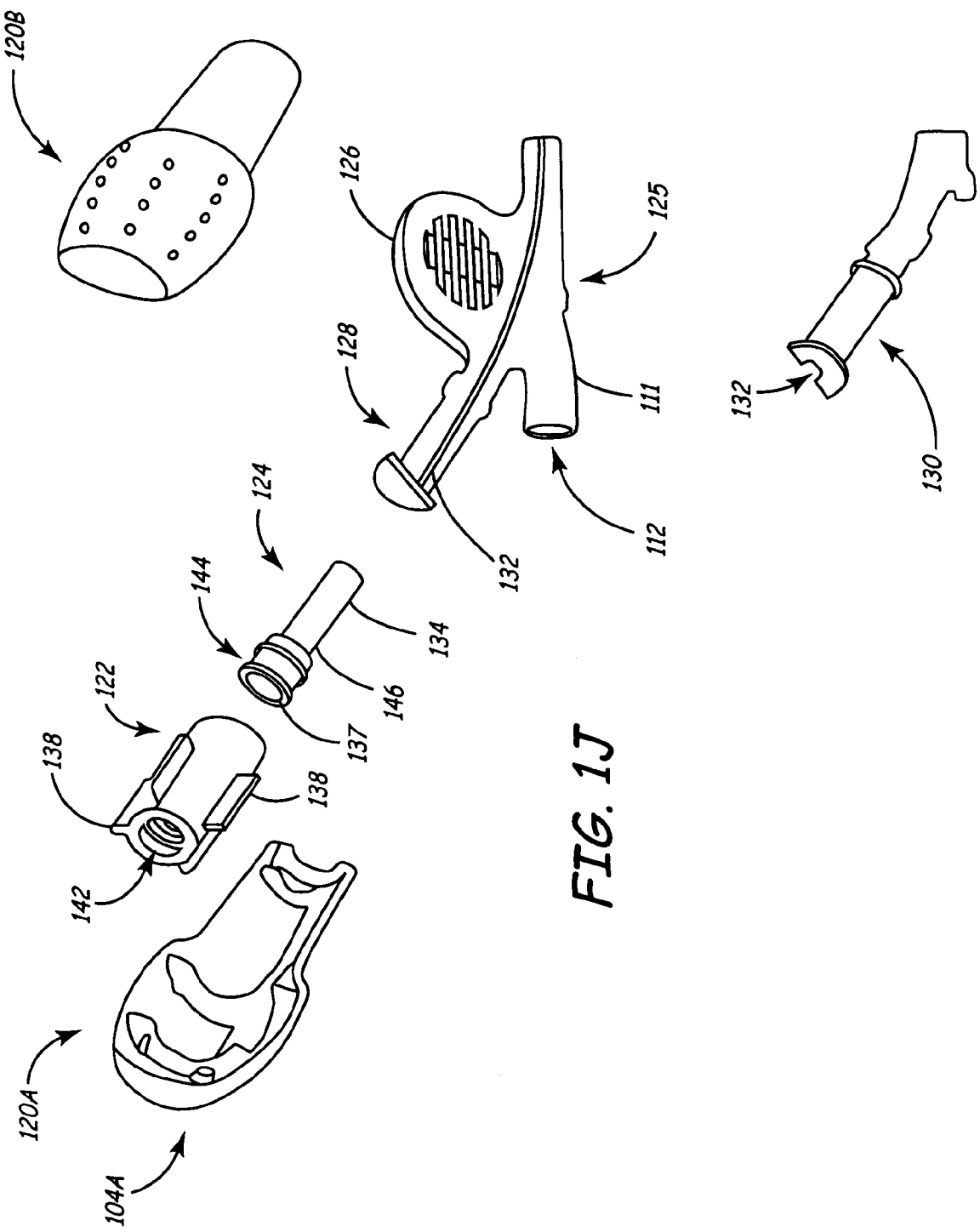
FIGS. 1J and 1K are exploded perspective views of a handle depicting various sub-components of the handle.
Figure 1K:
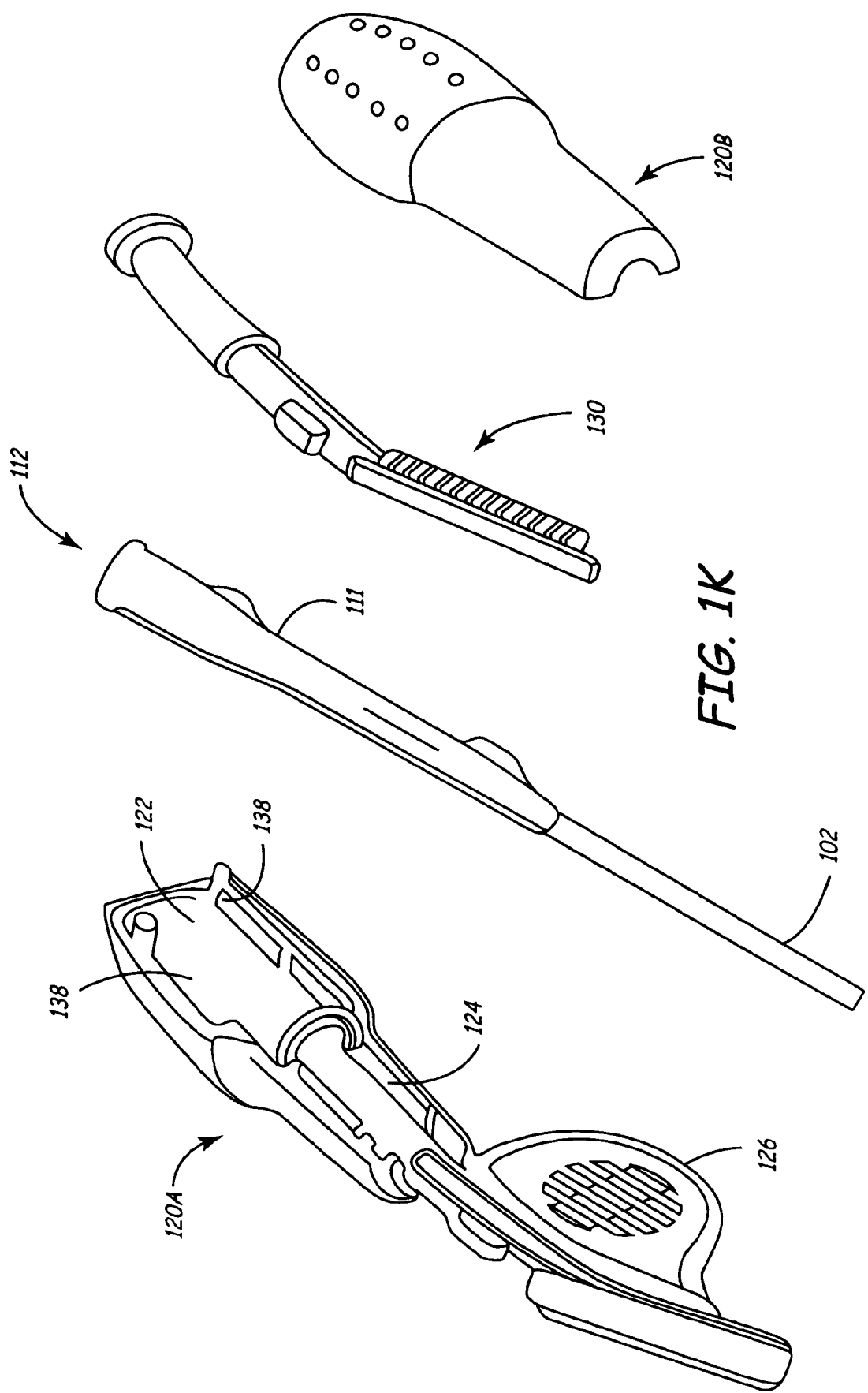
Figure 1L:
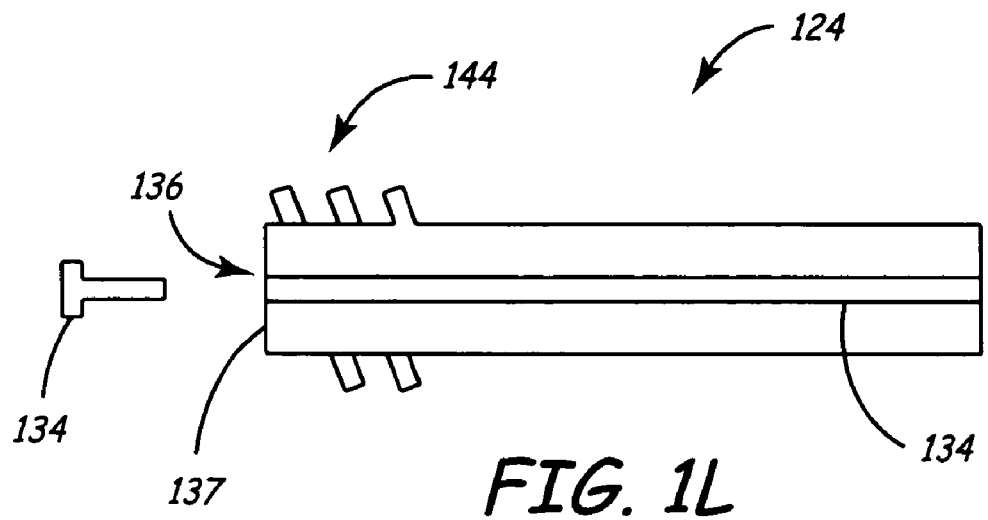
FIG. 1L is a cross-sectional side view of a slide screw according to the present invention.

FIGS. 1G–1L depict various views of one embodiment of the handle 104 of the catheter 100. More particularly, FIG. 1G is an enlarged side view of the handle 104. FIG. 1H is a cross-sectional side view of the handle 104 with the articulatable tip 105 in a straight or extended position. FIG. 1I is a cross-sectional view of the handle 104 with the tip 105 in its fully articulated position. FIGS. 1J and 1K are exploded perspective views of the handle 104 depicting various sub-components of the handle assembly. FIG. 1L is a cross-sectional side view of the slide screw 124 of the present invention.

As illustrated in FIGS. 1G–1L, the handle 104 generally includes handle halves 120A, 120B, a slide nut 122, a slide screw 124, a hub assembly 125, a gripping paddle 126, a hub top 128, a hub bottom 130 and a slide guide 132. Also depicted is the proximal opening 112 in the shaft 102. The handle halves 120A, 120B may be secured together by a variety of techniques, e.g., they may be bolted together.

As shown in FIGS. 1H and 1I, the hub assembly 125 has a lumen 133 that is formed therein. The lumen 133 is adapted to have the pull wire 116 positioned therein. As shown in FIG. 1L, the pull wire 116 will extend through a central opening 134 in the slide screw 124 and be coupled thereto by a pin 135 positioned in an opening 136 on the proximal end 137 of the slide screw 124. The slide nut 122 has a plurality of tabs 138 that are adapted to nest within recesses 140 formed in the handle halves 120A, 120B. The slide nut 122 has a plurality of internal threads 142 that extend throughout its length. The internal threads 142 are adapted to mate with external threads 144 on the slide screw 124. The generally rectangular body 146 of the slide screw 124 is adapted to be positioned within the slide guide 132 formed in the hub top 128 and the hub bottom 130. The slide body 146 and slide guide 132 are sized such that there is a clearance fit between the parts when mated, e.g., a clearance on the order of 0.002–0.004 inches on all sides.

The various components depicted in FIGS. 1G–1L may be of a molded construction, and they may be comprised of a variety of materials, e.g., acrylonitrile butadiene styrene (ABS), polycarbonate (PC), polyetherimide (PEI), etc. When assembled, the top hub 128 and the bottom hub 130 may be joined together by an ultrasonic welding process. The handle halves 120A, 120B may be joined together by a fastener, such as a screw or bolt. The shaft housing 111 may be secured to the hub assembly 125 by an appropriate adhesive material.

When assembled, the handle 104 may be actuated in a rotational direction, as indicated by arrow 150 in FIG. 1G, or in a translational or linear direction, as indicated by the arrow 152. Movement of the handle 104 in either direction will cause the tip 105 to move. The greater the movement, the greater the deflection of the tip 105. During rotational movement of the handle 104, the slide nut 122 is rotated due to the relationship between the tabs 138 on the slide nut 122 and the recesses 140 in the handle halves 120A, 120B. In turn, this rotation causes the threaded end 144 of the slide screw 124 to advance within the slide nut 122 toward the proximal end 104A of the handle 104, thereby exerting a pulling force on the pull wire 116 coupled to the slide screw 124 and deflecting the articulatable tip 105.

A similar deflection of the tip 105 may be accomplished by pulling on the handle 104 in the direction indicated by the arrow 152. A tab 134 on the body 146 of the slide screw 124 limits the extent of the travel allowed by the slide screw 124. The tab 134 is positioned in a recess (not shown) formed in the slide guide 132. A combination of rotational and translational movement of the handle 104 may be used to manipulate the tip 105 and, more particularly, the distal opening 109 of the shaft 102 to the desired location within the heart. In FIG. 1H, the tip 105 of the catheter 100 is fully extended. In this position, the threads 144 on the slide screw 124 are located near the distal end 159 of the slide nut 122. In contrast, in FIG. 1I, the tip 105 is in its fully articulated position. In that situation, the threads 144 on the slide screw 124 are positioned near the proximal end 160 of the slide nut 122.

The gripping paddle 126 is provided as an additional means for holding or manipulating the catheter shaft 102, e.g., pushing or pulling, during a surgical procedure. Additionally, the gripping paddle 126 may be used to hold the catheter 100 as it is being split when being removed from a patient.

One illustrative embodiment of a lead 200 that may be used with the present invention is depicted in FIGS. 2A–2G. FIG. 2A is a schematic diagram of a lead that may be used with the present invention. The lead 200 depicted therein is a bi-polar co-axial lead design that has a very small diameter (less than approximately 5 French (0.065")). More particularly, as illustrated in FIG. 2A, the lead 200 includes a distal portion 202, an anchoring sleeve 204, and a proximal portion 206. The overall length of the lead 200 may vary, e.g., from approximately 25–40 inches.

The distal portion 202 of the lead 200 will be described with reference to FIGS. 2B–2N. FIG. 2B is a sectional view of a distal portion of the lead of FIG. 2A. As illustrated in FIG. 2B, the distal portion 202 of the lead 200 includes an inner conductor 208, an inner layer of insulation 210, a conductor coil 212, an outer layer of insulation 214, an electrode ring 216, a spacer 218, and a helical screw 220. The inner conductor 208 is coupled to the helical screw 220 via a weld core crimp sleeve 222. Ultimately, as described more fully below, the lead 200 may be rotated to anchor the helical screw 220 into a patient's heart. Note that the helical screw 220 is provided by way of example only, as other types of active fixation devices, e.g., barbs, or passive fixation devices may be employed with the lead of the present invention. Thus, the present invention should not be considered as limited to the helical screw 220 depicted in the drawings unless such limitation is clearly set forth in the appended claims.

Although not depicted in the attached figures, an insulating layer or coating formed of a fluoropolymer, e.g., ETFE, PTFE, is formed on the outside of the inner conductor 208. In the case where the coating is ETFE, the coating may have a thickness of approximately 0.002–0.006 inches. This ETFE coating is a redundant layer of insulation that is useful in insulating the inner conductor 208. Note that the inner conductor 208 is a "solid" conductor, in that it does not have a lumen formed therein for a stylet.

In one illustrative embodiment, the inner conductor 208 is a 7×7 regular, right lay wire cable formed of a cobalt-nickel-chromium-molybdenum alloy (UNS R 30035) material. The inner insulation layer 210 may be formed of a variety of materials, e.g., silicone or polyurethane, and may have an inner diameter of approximately 0.010–0.018 inches and an outer diameter of approximately 0.018–0.030 inches. In one illustrative embodiment, the inner insulation layer 210 is extruded over the fluoropolymer coated inner conductor 208. This technique is less time-consuming than prior art techniques involving, for example, dilating the inner insulation layer 210 and, thereafter, positioning inner insulation layer 210 over the coated inner conductor 208. The fluoropolymer coating, e.g., ETFE, may be subjected to a plasma treatment to improve the surface texture of the outer surface of the ETFE coating prior to extruding the inner insulation layer 210 over the ETFE coated inner conductor 208.

The conductor coil 212 may be formed of a variety of materials and structures. In one illustrative embodiment, the conductor coil 212 is a five filar, right hand wound coil formed of 0.004 inch diameter wire formed of a cobalt-nickel-chromium-molybdenum alloy (UNS R 30035) material. The outer layer of insulation 214 may be formed of a variety of materials, e.g., silicone, polyurethane. In one illustrative embodiment, the outer insulation 214 is formed of polyether urethane tubing having an outside diameter of approximately 0.054 inches and an inside diameter of approximately 0.044 inches. That is, the distal portion 202 of the lead 200 may have a very small outside diameter, i.e., less than 4.5 French, due, at least in part, to the absence of a stylet lumen within the lead 200. The electrode ring 216 may also be formed of a variety of materials, and in one illustrative embodiment, the electrode ring 216 is formed of a platinum/iridium alloy (90/10), for example. The weld core 222 may be formed of a variety of materials, such as a platinum/iridium alloy (90/10). The spacer 218 may also be formed of a variety of materials, e.g., urethane.

FIGS. 2C and 2D are, respectively, a cross-sectional side view and end view of the spacer 218. FIGS. 2E, 2F and 2G are, respectively, a perspective view, a cross-sectional side view, and an end view of the weld core 222. As illustrated in FIGS. 2C–2D, the spacer 218 includes a plurality of flat portions 219 formed therein that are adapted to engage flat portions 221 formed on the weld core crimp sleeve 222 (FIG. 2E) to prevent rotation of the inner assembly within the outer assembly as the helical screw 220 is affixed to the patient's heart.

As illustrated in FIG. 2E, the weld core crimp sleeve 222 has an opening 223 formed therethrough that serves as a view port to insure that the inner conductor 208 is properly positioned within the weld core crimp sleeve 222. The inner conductor 208 may be secured within the well core crimp sleeve 222 by crimping, in a normal fashion or as described below, for example. The helical screw 220 may also be formed of a variety of materials. In one illustrative embodiment, the helical screw 220 is formed of a platinum/iridium alloy (75/25). The geometry of the helical screw 220, e.g., length, pitch, etc., may be varied as a matter of design choice.

Figure 2M:
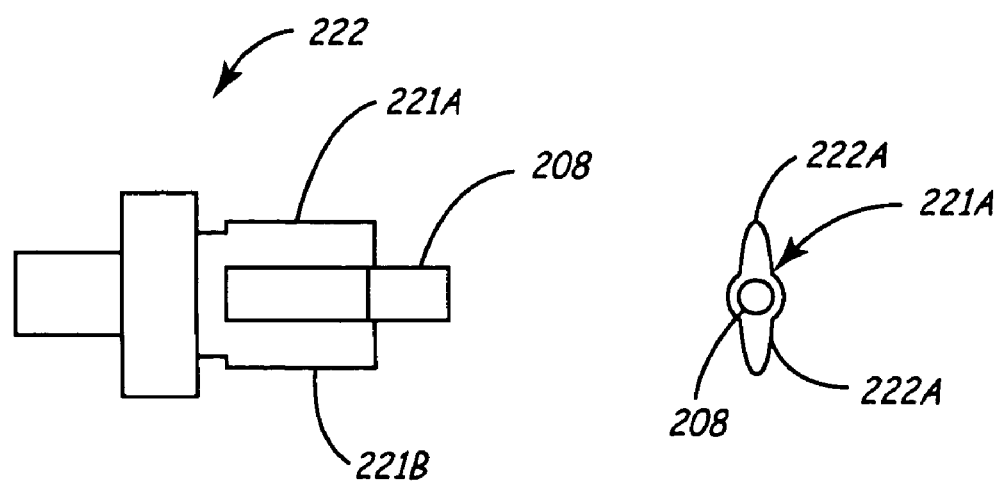
FIG. 2M is a side view of a weld core crimp sleeve of a lead according to the present invention.
Figure 2N:
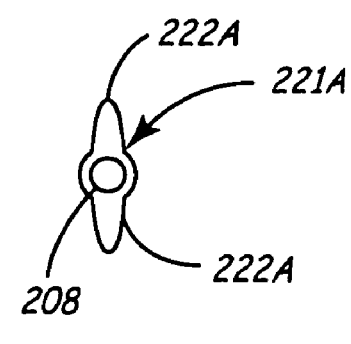
FIG. 2N is an end view of a weld core crimp sleeve of a lead according to the present invention.

FIG. 2M is a side view of a weld core crimp sleeve of a lead according to the present invention. FIG. 2N is an end view of a weld core crimp sleeve of a lead according to the present invention. In an alternative embodiment, as illustrated in FIGS. 2M and 2N, in lieu of the weld core crimp sleeve 222 being provided with the anti-rotation flat portions 221, the crimp formed along a proximal barrel 221A of the weld core crimp sleeve 222 to fixedly position the inner conductor 208 within a receiving portion 221B formed within the proximal barrel 221 to receive the inner conductor 208 results in the formation of protrusions 222A. In this embodiment, an adhesive backfill may be positioned between the spacer 218 and the protrusions 222A to prevent rotation therebetween. Alternatively, the spacer 218 may be provided with mating internal surfaces (not shown) to mate with the protrusions 222A to prevent rotation therebetween.

FIG. 2H is a cross-sectional side view of an illustrative electrode ring 216 that may be employed with the present invention. The conductor coil 212 is coupled to the end 219 of the electrode ring 216 by welding. The electrode ring 216 has an opening 217 formed therein that allows for insertion of adhesive and/or additional sealing materials to better seal the lead 200.

In one illustrative embodiment, the helical screws 220 and/or the electrode ring 216 may have a titanium nitride coating (not shown) formed thereon. The titanium nitride coating may be formed by a sputtering or other deposition process, and it may have a thickness ranging from approximately 2–20 microns. In effect, the titanium nitride coating acts to increase the surface area of the coated parts, thereby tending to reduce polarization effects when the device is operational. Additionally, with the presence of the titanium nitride coating, a steroid, such as DSP (dexamethasone sodium), DXAC (dexamethasone acetate) and/or Beclomethosone, may be added to the coated components. This is made possible due to the micro structure of the titanium nitride coated components that allow the steroid to be, at least to some degree, housed within its structure. If employed, this technique may result in the reduction and/or elimination of the need or use of so-called monolithic controlled release devices (MCRD) whereby steroid material was mixed with a silicone or urethane material and positioned adjacent the end of the lead. Of course, a titanium nitride coating is not required to practice the present invention in that the surface of the helical screw 220 and the electrode ring 216 may have a polished surface or it may have a planarized helix surface. Moreover, an MCRD device may be employed in addition to coating the helical screw 220 and/or the electrode ring 216.

FIGS. 2I, 2J and 2K are, respectively, a perspective view, a cross-sectional side view and an end view of one illustrative embodiment of the anchoring sleeve 204 that may be used with the present invention. As illustrated therein, the anchoring sleeve 204 includes a body 230, a plurality of tabs 232, an opening 233 extending through the body 230 of the anchoring sleeve 204, a distal opening 234, a proximal opening 236, and a plurality of body openings 238. The anchoring sleeve 204 may be formed of a variety of materials, e.g., a molded silicone rubber. In general, the distal portion 202 of the lead 200 will be positioned with the opening 233 in the anchoring sleeve 204. The projections 235 within the opening 233 of the anchoring sleeve 204 provide an interference fit with the distal end 202 of the lead 200 as it is positioned within the opening 233. That is, the anchoring sleeve 204 may be moved along the axial length of the distal end 202 of the lead 200. Ultimately, as described more fully below, once the helical screw 220 is properly fixed in the heart, the distal portion 202 may be coupled to the anchoring sleeve 204 by positioning portions of the distal portion 202 of the lead through the body openings 236 in the anchoring sleeve 204, and suturing those portions to the anchoring sleeve 204. Thereafter, the anchoring sleeve 204 may be sutured at an appropriate location within the patient's body.

Figure 2L:
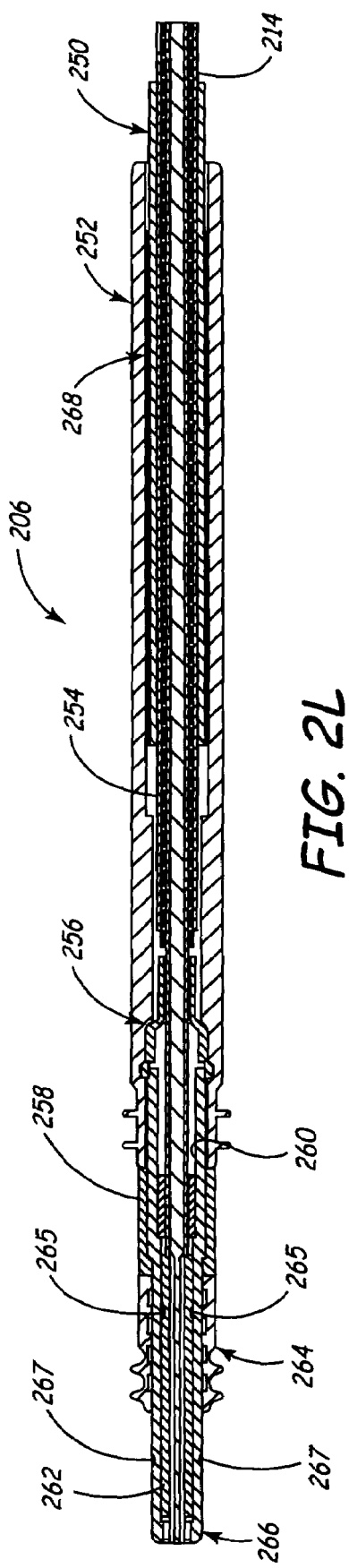
FIG. 2L depicts an illustrative embodiment of a proximal portion of a lead according to the present invention.
Figure 2B:
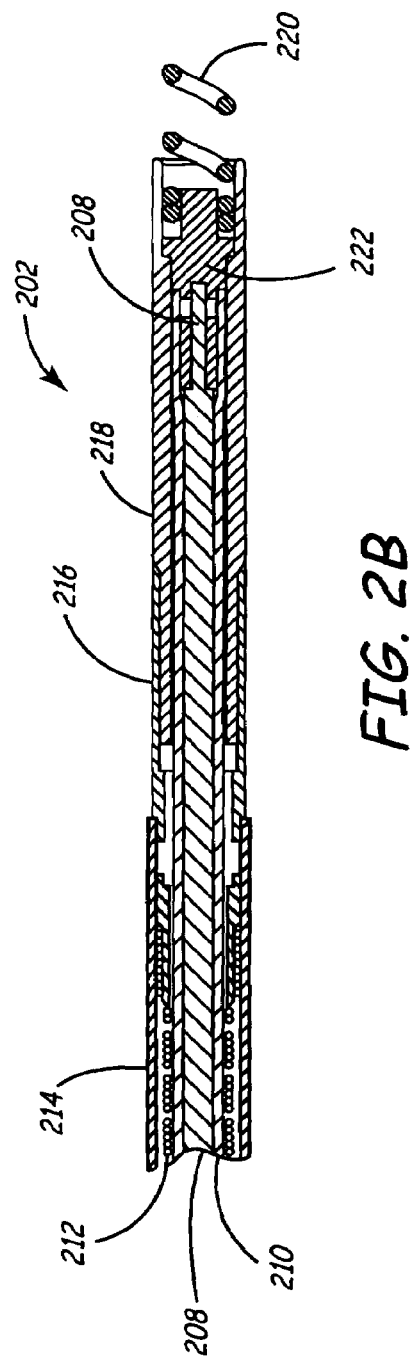
FIG. 2B is a sectional view of a distal portion of the lead of FIG. 2A.

FIG. 2L depicts an illustrative embodiment of the proximal portion 206 of the lead 200. As shown therein, the proximal portion 206 includes an inner tube 250, a connector sleeve 252, an insulating tube 254, a welding sleeve 256, a connector ring 258, a retainer 260, a connector pin 262, a seal 264, and a cap 266. The proximal portion 206 may include a label 268 containing information such as the manufacturer, model number, and size of the lead 200.

The inner tube 250 may be formed of a variety of materials, e.g., silicone, polyurethane, etc., and its size may vary. For example, in one illustrative embodiment, the inner tube 250 is formed of silicone and has an outer diameter of approximately 0.08 inches and an inner diameter of approximately 0.052 inches. Similarly, the connector sleeve 252 may be formed of a variety of materials, e.g., silicone, polyurethane, etc., and its size may also vary. In one illustrative embodiment, the connector sleeve 252 is formed of silicone and has an outer diameter of approximately 0.125 inches. The inner diameter of the connector sleeve 252 may vary at multiple locations to accommodate the positioning of various components therein.

As shown in FIG. 2L, the conductor coil 212 is welded to the welding sleeve 256. In turn, the welding sleeve 256 is welded to the connector ring 258. The welding sleeve 256 and conductor ring 258 may be formed of a variety of materials. In one illustrative embodiment, the welding sleeve 256 and the connector ring 258 are formed of type 316L stainless steel. The combination of the connector ring 258, welding sleeve 256, and conductor coil 212 are used to sense signals received by the electrode ring 216. The inner conductor 208 extends through the welding sleeve 256 and is positioned within the connector pin 262 and secured thereto by crimping, as indicated by the arrow 265. The connector pin 262 may be formed of a variety of conductive materials. In one illustrative embodiment, the connector pin 262 is formed of type 316L stainless steel. The cap 266 is positioned over the connector pin 262 and secured thereby by crimping, as indicated by the arrow 267. The cap 266 may be formed of a variety of materials, such as type 316L stainless steel. The retainer 260 and seal 264 may be formed of a variety of insulating materials, e.g., silicone, polyurethane, etc.

The catheter/lead combination of the present invention may be introduced into a patient by a variety of known techniques. For example, in one technique, a combined needle and sheath structure (not shown) are used to locate the desired entry point vein. When the proper vein has been located, a syringe is used to draw blood to confirm that the desired vein has been perforated. Thereafter, the sheath is extended further into the vein, and the needle is withdrawn. The catheter shaft 102 is then routed through the sheath into the vein and guided to the desired area of the heart, e.g., the right atrium, the right ventricle, etc. The physician, using radiographic observation techniques, may then actuate the handle 104 to position the articulatable tip 105 of the catheter 100 at the desired location within the heart. Thereafter, the physician may advance and rotate the lead 200 to fixate the helical screw 220 into engagement with the heart where the fixation device is a helical screw 220. Although the distal portion 202 of the lead 200 of the present invention has a very small diameter, it nevertheless provides the necessary rigidity and torqueability to enable it to be used to affix the helical screw 220 to the patient's heart. After the helical screw 220 is affixed to the wall, the catheter 100 may be slightly withdrawn away from the wall, and a gentle tension is applied to the lead 200 to insure sufficient mechanical attachment of the helical screw 220 to the patient's heart. Thereafter, the catheter 100 may be removed from the patient. The catheter 100 may be slit with an appropriate cutting tool.

The catheter 100 with the articulatable tip 105 of the present invention provides a surgeon with a controllable means to more precisely place leads in the heart at a variety of locations within the heart. That is, the articulatable tip 105 may be moved to a variety of locations by actuating the handle 104, i.e., by rotational or translational movement of the handle 104. Simply put, the articulatable tip 105 allows the surgeon to, in controlled fashion, locate the distal opening 109 of the shaft 102 at a variety of different locations within the heart.

Figure 3:
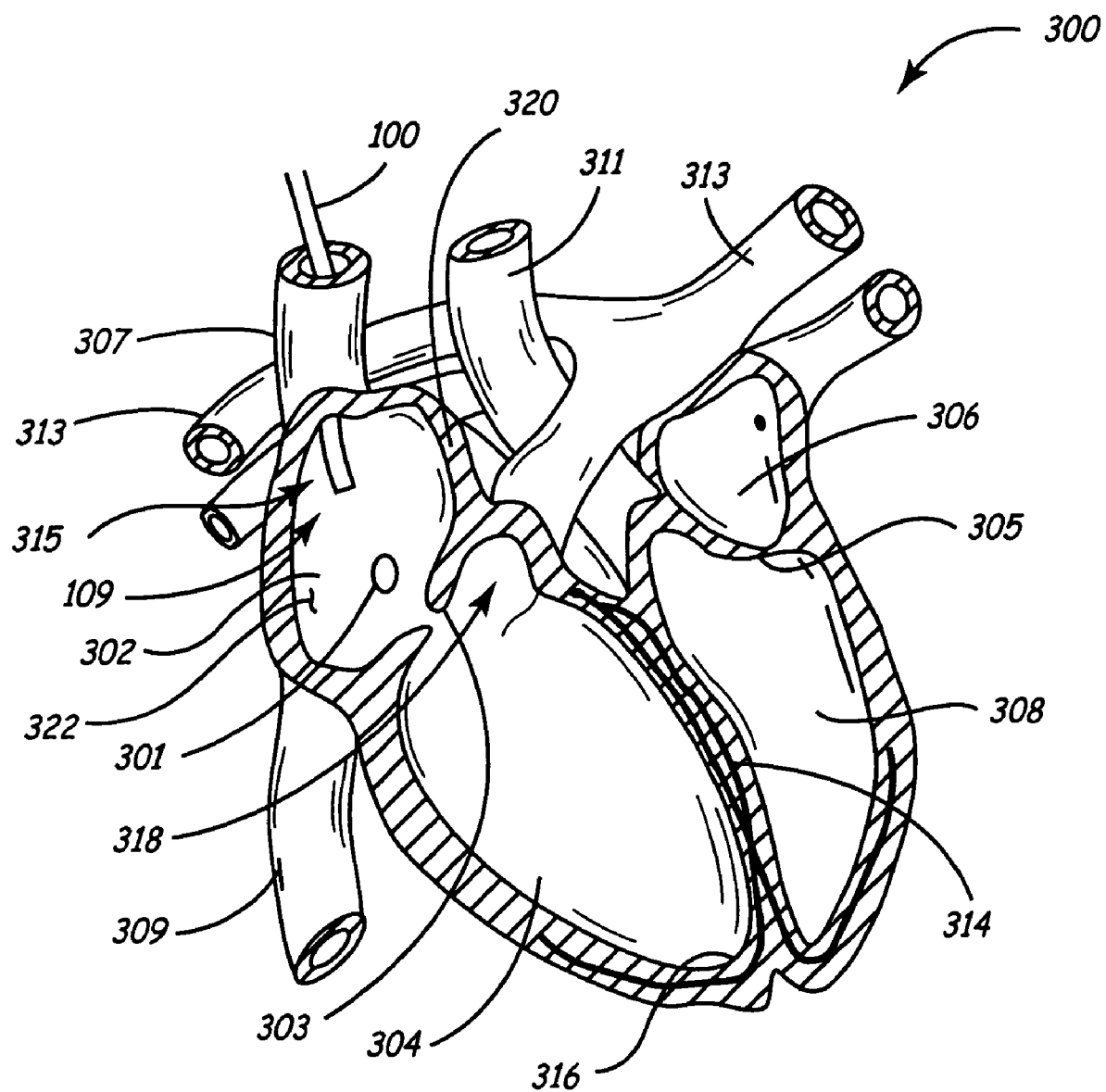
FIG. 3 depicts an illustrative partial cross-sectional view of the human heart.

With reference to FIG. 3, the heart 300 generally includes four chambers, the right atrium 302, the right ventricle 304, the left atrium 306 and the left ventricle 308. Some of the additional structure of the heart depicted in FIG. 3 includes the coronary sinus ostium 301 that leads to the coronary sinus (not shown), the tricuspid valve 303, and the mitral valve 305. FIG. 3 also depicts several major veins and arteries that are used in routing blood to and from the heart 300. For example, FIG. 3 depicts the superior vena cava 307, the inferior vena cava 309, the aorta 311 and the pulmonary artery 313. The distal opening 109 of the catheter 100 is depicted in the right atrium 302 for purposes of illustration only, as distal opening may be positioned in virtually any area of the heart 300.

In general, the heart's nervous system controls the manner in which the heart's pumping activities are performed. For example, electrical impulses first pass from the sinoatrial node (not shown) through both the right and left atrium 302, 306, causing them to contract. The atrioventricular node (not shown) then delays the electrical signals before passing them through the fibers in the heart called the Bundle of His 314. The electrical impulses then spread into the right and left ventricles 304, 308 causing them to contract.

By use of the present invention, leads may be readily and reliably positioned at a variety of locations within the heart 300 in a controlled fashion. For example, the catheter 100 of the present invention may be used in placing a lead at traditional sites, e.g., the apex 316 of the right ventricle, the atrial appendage 315, or in one of the cardiac veins accessible via the coronary sinus ostium 301, e.g., the great cardiac vein, the middle cardiac vein, the posterial lateral cardiac vein, the anterial lateral cardiac vein, etc. In addition, the present invention may allow accurate and reliable placement of leads at a variety of alternative sites, e.g., the Bundle of His 314, right ventricular outflow tract (RVOT) 318, the interatrial septum 320, the lateral wall 322 of the right atrium 302, interventricular septum 324, etc. Simply put, the catheter 100 with the articulatable tip 105 allows controlled placement of leads at a variety of locations within the heart 300.

As medical research continues to advance, the present invention will be useful in allowing surgeons to place leads in a reliable and controlled fashion in locations determined to be most appropriate for delivery of therapy to the heart.

As stated above, the present invention may be used to position leads in the heart that will be used in providing a variety of different types of therapy to the heart, e.g., pacing, defibrillation, etc. Thus, the inventive methods disclosed herein should not be considered as limited to the delivery of any particular type of therapy to the heart unless such limitations are expressly recited in the appended claims.

One illustrative method of the present invention includes providing a catheter 100 having a shaft 102, an articulatable tip 105 and an actuatable handle 104, the shaft 102 having a distal opening 109 and a lumen 110 that is adapted to have a lead positioned therein, inserting the distal opening 109 of the catheter shaft 102 into the heart, and positioning the distal opening 109 of the shaft 102 at a desired location within the heart by actuating the handle 104 so as to manipulate the articulatable tip 105 of the catheter 100. In further embodiments, the present invention is directed to the use of a catheter 100 having a bitumen construction, i.e., lumen 110 (for the lead 200) and lumen 114 (for the pull wire 116). In this embodiment, the actuation of the handle 104 exerts a pulling force on the pull wire 116 positioned in the pull wire lumen 114. In even further embodiments, the methods disclosed herein may further include positioning the distal opening 109 of the shaft 102 at a desired location of the heart to enable placement of a lead in at least one of an apex of a right ventricle of the heart, a right atrial appendage of the heart, a right ventricle outflow tract of the heart, a Bundle of His of the heart, an interatrial septum of the heart, the interventricular septum of the heart, a lateral wall of a right atrium of the heart, and a cardiac vein coupled to a coronary sinus of the heart.

Another aspect of the present invention is directed to a novel lead that may be used to deliver electrical signals to and/or receive electrical signals from a human heart. In general, the lead 200 includes a solid inner conductor 208, a fixation device electrically coupled to the inner conductor 208, the fixation device having a titanium nitride coated surface, a steroid applied to the titanium nitride surface of the fixation device, and at least one layer of insulation positioned around the inner conductor 208. The lead 200 further includes a conductive coil 212 positioned around and insulated from the inner conductor 208, an electrode ring 216 positioned around and electrically isolated from the inner conductor 208, the electrode ring 216 being electrically coupled to the conductive coil 212, and an insulating spacer 218 positioned between and electrically isolating the electrode ring 216 and the fixation device. In one particularly illustrative embodiment, the fixation device is a helical screw 220. Moreover, in further embodiments, the electrode ring 216 may have a titanium nitride coated surface, and a steroid may be applied to that surface.

Yet another aspect is directed to a method of forming a lead that may be inserted into a patient's heart. In one illustrative embodiment, the method includes providing a cabled inner conductor, coupling a fixation device to the solid inner conductor by welding the fixation device to a welding core that is coupled to the solid inner conductor, forming a titanium nitride coating on a surface of the fixation device, applying a steroid to the titanium nitride coated surface of the fixation device, forming at least one layer of insulation around the inner conductor, positioning a conductive coil around the at least one layer of insulation, positioning an electrode ring around the inner conductor, the electrode ring being electrically isolated from the inner conductor and electrically coupled to the conductive coil, and positioning an insulating spacer between the electrode ring and the fixation device.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A lead for delivering electrical signals to and receiving electrical signals from a patient, comprising:
    a solid inner conductor;
    a distal electrode electrically coupled to the inner conductor, the distal electrode having a coated surface;
    an anti-inflammatory agent applied to the distal electrode;
    at least one layer of insulation positioned around the inner conductor;
    a conductive coil positioned around and insulated from the inner conductor;
    a proximal electrode positioned around and electrically isolated from the inner conductor, the proximal electrode being electrically coupled to the conductive coil; and
    an insulating spacer positioned between and electrically isolating the proximal electrode and the distal electrode, wherein the insulating spacer includes a first plurality of engaging portions, the lead further comprising a coupling portion coupling the solid inner conductor within the lead and having a second plurality of engaging portions adopted to engage the first plurality of engaging portions to prevent rotation of the distal electrode within the lead.

2. A lead for delivering electrical signals to and receiving electrical signals from a patient, comprising:
    a solid inner conductor;
    a distal electrode electrically coupled to the inner conductor, the distal electrode having a coated surface;
    an anti-inflammatory agent applied to the distal electrode;
    at least one layer of insulation positioned around the inner conductor;
    a conductive coil positioned around and insulated from the inner conductor;
    a proximal electrode positioned around and electrically isolated from the inner conductor, the proximal electrode being electrically coupled to the conductive coil; and
    an insulating spacer positioned between and electrically isolating the proximal electrode and the distal electrode, wherein the solid inner conductor includes an outer portion, the lead further comprising a fluoropolymer layer positioned along the outer portion.

3. The lead of claim 2, wherein the solid inner conductor is a 7×7 wire cable.

4. The lead of claim 2, wherein the distal electrode has a steroid applied to the coated surface.

5. The lead of claim 2, wherein the distal electrode is one of an active fixation device and a passive fixation device.

6. The lead of claim 2, wherein the distal electrode is a helical screw.

7. The lead of claim 2, further comprising a coupling portion coupling the solid inner conductor within the lead and having a plurality of engaging portions to prevent rotation of the distal electrode within the lead, wherein the coupling portion forms a receiving portion receiving the solid inner conductor and the plurality of engaging portions are formed by crimping the coupling portion against the solid inner conductor positioned within the receiving portion.

8. The lead of claim 2, wherein the distal electrode is formed of a platinum/iridium alloy.

9. The lead of claim 2, wherein the anti-inflammatory agent is comprised of at least one of DSP (dexamethasone sodium phosphate), DXAC (dexamethasone acetate) and Beclomethosone.

10. The lead of claim 2, wherein the conductive coil is formed of a nickel-cobalt chromium-molybdenum alloy.

11. The lead of claim 2, wherein the proximal electrode is a ring formed of a platinum/iridium alloy.

12. The lead of claim 2, wherein the insulating spacer is formed of urethane.

13. The lead of claim 2, wherein the fluoropolymer layer is formed of Ethylene Tetrafluoroethylene (ETFE) and has a thickness of approximately 0.002–0.006 inches.

14. The lead of claim 2, wherein the proximal electrode is a coil formed of a platinum/iridium alloy.

15. The lead of claim 2, wherein the distal electrode coating is titanium nitride.

16. The lead of claim 15, wherein the titanium nitride coating on the distal electrode has a thickness of approximately 2–20 microns.

17. The lead of claim 2, wherein the at least one layer of insulation positioned around the inner conductor is formed of a fluoropolymer coating positioned on the inner conductor and a layer of insulation formed of one of silicon and polyurethane positioned around the fluoropolymer coating.

18. The lead of claim 17, wherein the layer of insulation is extruded around the fluoropolymer coating and the inner conductor.

19. The lead of claim 2, wherein the proximal electrode has a titanium nitride coated surface.

20. The lead of claim 19, wherein the titanium nitride coating on the proximal electrode has a thickness ranging from approximately 2–20 microns.

21. A lead for delivering electrical signals to and receiving electrical signals from a patient, comprising:
    a solid inner conductor;
    a helical screw fixation device electrically coupled to the inner conductor, the helical screw fixation device having a first titanium nitride coated surface;
    a steroid applied to the titanium nitride coated surface of the helical screw fixation device;
    a fluoropolymer coating positioned around the inner conductor, wherein the fluoropolymer coating is one of Ethylene TetraFluoroEthylene (ETFE) and PolyTetraFluoroEthylene (PTFE);
    a layer of insulation positioned around the fluoropolymer coating, wherein the layer of insulation is one of silicone and polyurethane;
    a conductive coil positioned around the layer of insulation, the conductive coil being electrically isolated from the inner conductor;
    an electrode ring positioned around and electrically isolated from the inner conductor, the electrode ring having a second titanium nitride coated surface, the electrode ring being electrically coupled to the conductive coil; and
    an insulating spacer positioned between and electrically isolating the electrode ring and the fixation device.

22. The lead of claim 21, wherein the solid inner conductor is a 7×7 wire cable.

23. The lead of claim 21, wherein the insulating spacer includes a first plurality of engaging portions, the lead further comprising a coupling portion coupling the solid inner conductor within the lead and having a second plurality of engaging portions adopted to engage the first plurality of engaging portions to prevent rotation of the distal electrode within the lead 24. The lead of claim 21, further comprising a coupling portion coupling the solid inner conductor within the lead and having a plurality of engaging portions to prevent rotation of the distal electrode within the lead, wherein the coupling portion forms a receiving portion receiving the solid inner conductor and the plurality of engaging portions are formed by crimping the coupling portion against the solid inner conductor positioned within the receiving portion.

25. The lead of claim 21, wherein the helical screw is formed of a platinum/iridium alloy.

26. The lead of claim 21, wherein the first titanium nitride coating has a thickness of approximately 2–20 microns.

27. The lead of claim 21, wherein the steroid is one of DSP (disodiumphosphate), DXAC (acetate) and Beclomethosone.

28. The lead of claim 21, wherein the layer of insulation is extruded around the fluoropolymer coating and the inner conductor.

29. The lead of claim 21, wherein the conductive coil is a cobalt-nickel-chromium-molybdenum alloy.

30. The lead of claim 21, wherein the electrode ring is a platinum/iridium alloy.

31. The lead of claim 21, wherein the second titanium nitride coating has a thickness ranging from approximately 2–20 microns.

32. A method of forming a lead for delivering electrical signals to and receiving electrical signals from a patient, comprising:
  coupling a fixation device to a solid inner conductor by welding the fixation device to a coupling device that is coupled to the solid inner conductor;
  forming a titanium nitride coating on a surface of the fixation device;
  applying a steroid to the titanium nitride coated surface of the fixation device;
  forming at least one layer of insulation around the inner conductor;
  positioning a conductive coil around the at least one layer of insulation;
  positioning an electrode ring around the inner conductor, the electrode ring being electrically isolated from the inner conductor and electrically coupled to the conductive coil; and
  positioning an insulating spacer between the electrode ring and the fixation device.

33. The method of claim 32, wherein the solid inner conductor is a 7×7 wire cable.

34. The method of claim 32, wherein the step of coupling comprises:
  inserting the solid inner conductor within the coupling device; and
  fixedly engaging the coupling device against the solid inner conductor, the fixedly engaging forming a plurality of engaging portions to prevent rotation of the fixation device within the lead.

35. The method of claim 32, wherein the titanium nitride coating is formed along a surface of the fixation device by sputter deposition.

36. The method of claim 32, wherein the steroid applied to the titanium nitride coated surface of the fixation device is one of DSP (disodiumphosphate), DXAC (acetate) and Beclomethosone.

37. The method of claim 32, wherein forming at least one layer of insulation around the inner conductor comprises:
  forming a fluoropolymer coating on the inner conductor; and
  extruding a layer of insulation formed of at least one of silicon and polyurethane around the fluoropolymer coating and the inner conductor.

38. The method of claim 32, wherein the electrode ring is formed of a platinum/iridium alloy around the inner conductor.

39. The method of claim 32 further comprising applying a steroid to the titanium nitride coated surface of the electrode ring.

40. The method of claim 32, wherein the insulating spacer is formed of urethane.

41. The method of claim 32, further comprising forming a titanium nitride coating on a surface of the electrode ring.

42. The method of claim 41, wherein the titanium nitride coating is formed on a surface of the electrode ring by sputter deposition.

43. The method of claim 41, wherein applying a steroid to the titanium nitride coated surface of the electrode ring comprises applying a steroid comprised of at least one of DSP (disodiumphosphate), DXAC (acetate) and Beclomethosone to the titanium nitride coated surface of the electrode ring.

* * * * *

UNITED STATES PATENT AND TRADEMARK OFFICE
CERTIFICATE OF CORRECTION

PATENT NO.         : 7,184,839 B2                                          Page 1 of 1
APPLICATION NO. : 10/318518
DATED              : February 27, 2007
INVENTOR(S)        : Clemens et al.

It is certified that error appears in the above-identified patent and that said Letters Patent is hereby corrected as shown below:

Title Pg, Item (75) Inventors: please change "Willim J. Clemens" to --William J. Clemens--.

Signed and Sealed this

Eighth Day of April, 2008

JON W. DUDAS
*Director of the United States Patent and Trademark Office*